United States Patent [19]

Alais

[11] 4,117,446

[45] Sep. 26, 1978

[54] DEVICES FOR PROBING BY ULTRASONIC RADIATION

[75] Inventor: Pierre M. Alais, Dampierre, France

[73] Assignee: Agence Nationale de Valorisation de la Recherche (A N V A R), Neuilly sur Seine, France

[21] Appl. No.: 807,921

[22] Filed: Jun. 20, 1977

Related U.S. Application Data

[63] Continuation-in-part of Ser. No. 629,599, Nov. 6, 1975.

[30] Foreign Application Priority Data

Jun. 18, 1976 [FR] France .................... 76 18640

[51] Int. Cl.² .................................... G01N 29/04
[52] U.S. Cl. ............................ 340/1 R; 340/5 H; 340/5 MP; 340/6 R; 343/17; 73/606; 73/607; 73/626; 73/628; 358/112; 128/2 V; 128/2.05 Z
[58] Field of Search ............... 358/110, 112; 340/1 R, 340/5 H, 5 MP, 6 TV; 343/17; 128/2 V, 2.05 Z; 73/606, 628, 607, 626, 67.8 R, 67.8 S

[56] References Cited

U.S. PATENT DOCUMENTS

| | | |
|---|---|---|
| 3,820,387 | 6/1974 | Grabendorfer .................... 73/626 |
| 3,856,985 | 12/1974 | Yokoi ............................... 358/112 |
| 3,911,730 | 10/1975 | Niklas .............................. 73/626 |
| 3,918,025 | 11/1975 | Koshikawa et al. ............... 73/626 |
| 3,953,825 | 4/1976 | Kimo et al. ....................... 73/626 |
| 4,019,169 | 4/1977 | Takamizawa ..................... 73/626 |

Primary Examiner—Robert L. Griffin
Assistant Examiner—Edward L. Coles
Attorney, Agent, or Firm—Ostrolenk Faber Gerb & Soffen

[57] ABSTRACT

N elementary transducers are distributed regularly along a line of scanning. An ultrasonic frequency receiver is associated with phase lag means. The distribution over $n$ successive elementary transducers of the phases corresponding to focusing at a predetermined distance or several successive distances from the line is stored. That distribution corresponds to several Fresnel zones. Switches first connect a generator to a group of $n'$ transducers corresponding to the central Fresnel zone of said stored distribution and later connect a group of $n$ transducers to the receiver direct and via the phase lag means according to the stored distribution(s). The groups of $n'$ and $n$ elementary transducers are shifted along the line at intervals of time. The phase lag means may consist of inverter means causing a phase angle of $\pi$.

9 Claims, 9 Drawing Figures

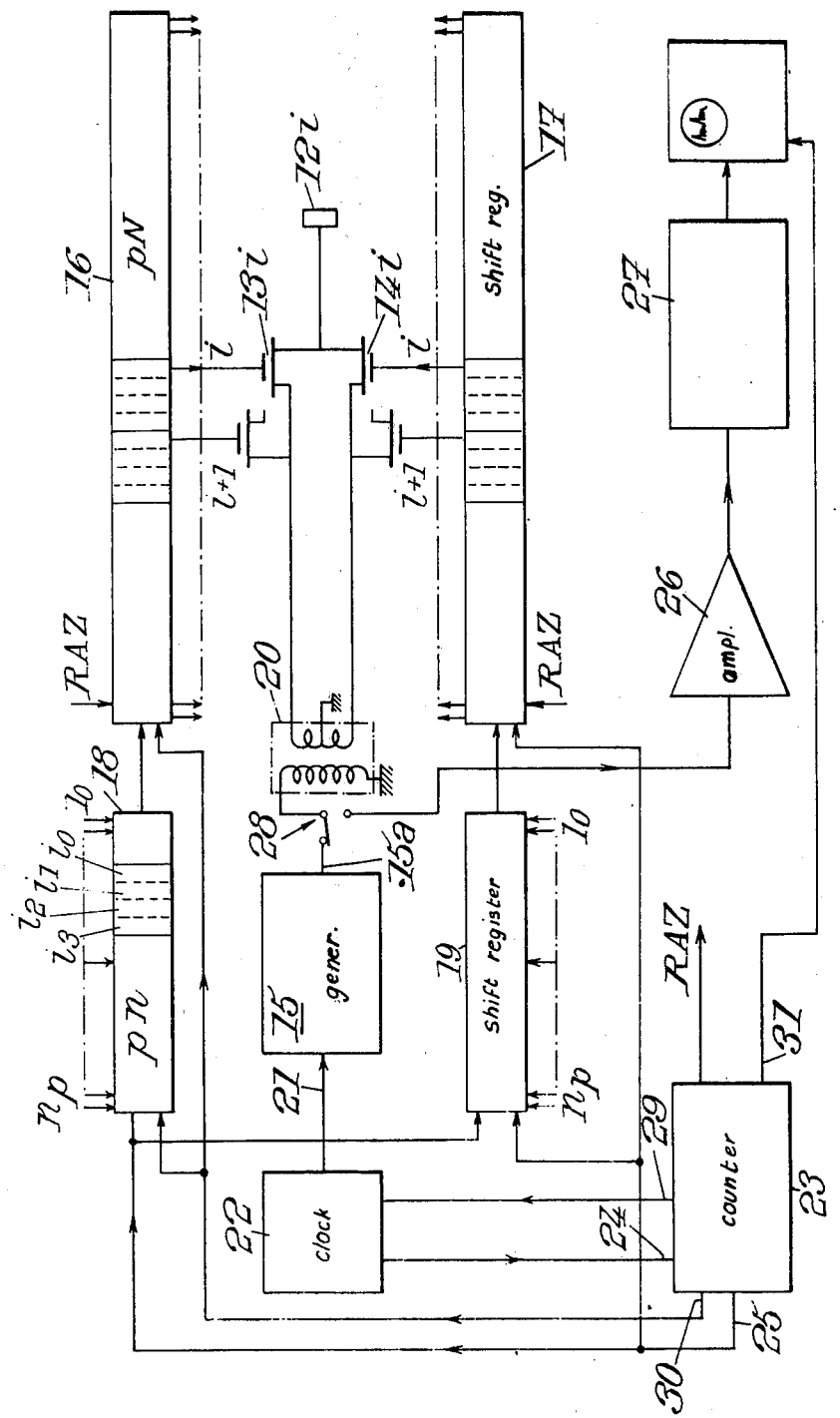

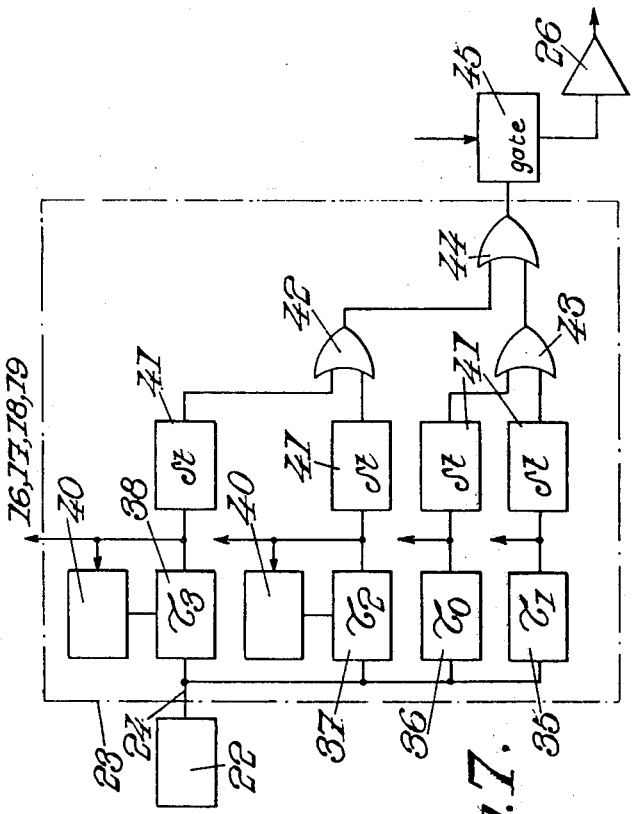
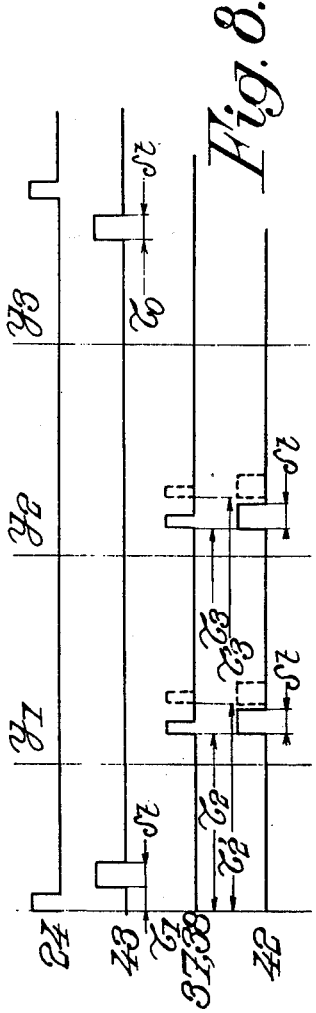
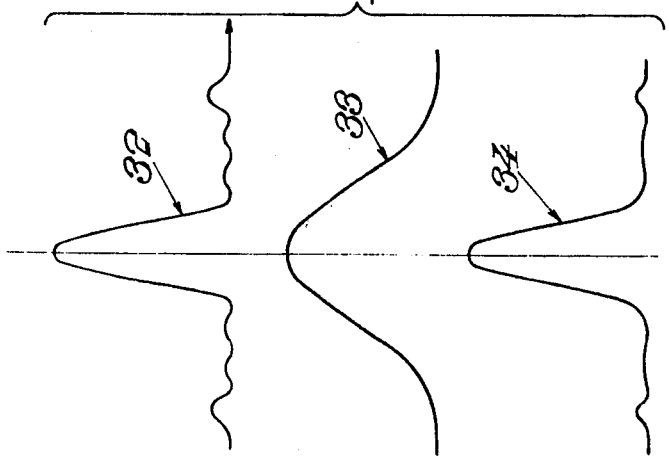

DEVICES FOR PROBING BY ULTRASONIC RADIATION

CROSS REFERENCES TO RELATED APPLICATIONS

This is a continuation-in-part of my copending application Ser. No. 629,599, filed Nov. 6, 1975 the subject matter of which is included in the present application by way of reference.

BACKGROUND AND SUMMARY OF THE INVENTION

The present invention relates to ultrasonic imaging with electronic scanning, enabling the exploration of a part or an organ to be analyzed, notably in a plan (C scan mode echography) or in depth (B mode echography).

Such an imaging device is capable of numerous applications, particularly in the field of medicine, in which field imaging by ultrasonic offers, over imaging by ionizing radiation (including X-rays), the great advantage of not subjecting the patient to harmful radiation.

Before defining the invention, it would seem desirable to recall some theoretical considerations which relate to the ultrasonic transmitters, although they apply just as well to receivers.

The energy of an ultrasonic beam transmitted to a medium by $n$ elementary transducers distributed along a direction Ox may be focused at a point M in front of O and at the distance $Y_M$ from the straight line on which the $n$ elementary transducers are distributed. If the radiation has a wave length $\lambda$ in the propagation medium concerned, each transducer of order $i$ must receive a signal whose phase lead with respect to the transducer placed at 0 is:

$$\phi_i = \pi x^2_i / \lambda y \tag{1}$$

$x_i$ being the abscissa of the transducer with respect to 0.

In other words, the complex amplitude $A^*_i$ of the signal applied to the elementary transducers of order $i$ must be:

$$A^*_i = A_o \exp(j\phi_i) \tag{2}$$

whose real part is:

$$A_o \cos \phi_i \tag{3}$$

and imaginary part is:

$$A_o \sin \phi_i \tag{4}$$

There have been described ultrasonic imaging devices in which pseudo-focusing is achieved by energizing simultaneously and in phase a group of elementary transducers whose cumulative length along Ox is $b = 2\sqrt{Y\lambda}$, i.e. corresponds to the first zone of the Fresnel representation. Resolution of such a system is poor. It has also been suggested to associate a generator and a receptor to each elementary transducer and to simulate the phase repartition of several successive Fresnel zones. The same successive elementary transducers are used for reception and for transmission, with the same distribution, corresponding to a plurality of even and odd Fresnel zones associated with the focussing being sought. Such a system is quite complex and expensive. In addition, the main central lobe which provides the required focussing is accompanied by secondary lobes which may be unfavorable when the target is highly reflective. For example, in the case of heart imaging by echography B the rear wall of the heart provides specular reflection and often alters the visualization of target reflecting less powerful echoes, which are located in the vicinity.

It is an object of the invention to provide an imaging device which overcomes the limitations of the prior art devices.

According to an aspect of the invention, there is provided a device for ultrasonic imaging with electronic scanning, having an array of N identical elementary transducers distributed at equal intervals along a scanning direction and operating at frequency $f$; a single signal generator for generating electrical signals; a single signal receiver for receiving and processing electrical signals; means for storing an electrical phase distribution signal representative of the phase distribution of $n$ signals associated with $n$ adjacent transducers of said array, $n$ being an integer greater than 1 and less than N, each said signal having a frequency $f$ and having any one of $m$ phases with respect to the remaining said $n$ signals ($m$ being an integer less than $n$), said electrical phase distribution signal being chosen such that said $n$ adjacent transducers focus energy at a point located at a predetermined distance from said array of transducers; switch means for simultaneously and temporarily applying said signal from said generator to a set of $n$ transducers in accordance with said phase distribution and subsequently for simultaneously and temporarily applying the echo signals from a set of those $n'$ transducers among the $n$ transducers which are closest to said point to said receiver; and sequencing means for causing said switch means to apply said signal to $n$ transducers at each of a plurality of successive times and to apply said echo signal to said receiver, each time to and from a set of $n$ and $n'$ transducers, respectively, which is shifted by at least one said transducer of said array of transducers, such that scanning occurs through said array.

$m$ will preferably be equal to two; then some of the transducers will receive the energy with a reference phase and the others energy which is 180° out of phase with the reference phase.

The number $n'$ is advantageously chosen to correspond with the first Fresnel zone of the phase distribution ensuring focussing at the predetermined distance. In other words, the $n'$ transducers connected for transmission (or reception) are the transducers which are located in the middle of the group of $n$ transducers and which are connected to the receiver (or generator) with the same phase during reception (or transmission). Thus the secondary lobes upon the transmission are almost completely suppressed. With reception (or transmission) continuing to take place at full aperture, the level of the sidelobes is lowered to an acceptable threshold and the signal is "apodized" with a diminution of the resolution which is only very slight.

According to a particular embodiment of the invention, the storage means include two shift registers having p.n positions, which store, in operation:

the first, in positions $1, p, 2p, \ldots, (n-1)p$, the location of those of the $n$ elementary transducers to be connected to the generator with the first phase; in the positions $2, p+1, \ldots, (n-1)p+1$, the location of those of the $n$ elementary transducers to be connected to the receiver with the first phase for achieving focussing at a first predetermined distance from the line; and if necessary, in a group or other groups of n positions, the location of the n elementary transducers to be connected to the receiver with the said first phase for achieving focussing or focussings at another predetermined distance or at other predetermined distances;

the second, in positions $1, p, 2p, \ldots, (n-1)p$, the location of those of the $n$ elementary transducers to be connected to the receiver with the second phase; in the positions $2, p+1, \ldots, (n-1)p+1$, the location of those of the $n$ elementary transducers to be connected to the receiver with the second phase for achieving focussing at a second predetermined distance from the line; and if necessary, in a group or other groups of $n$ positions, the location of the $n$ elementary transducers to be connected to the receiver with the said second phase for achieving focussing or focussings at the other predetermined distance or at other predetermined distances; a clock being provided for causing the shifting or the contents of the said registers and their transfer in series into two shift registers of N positions, each position controlling the switching means associated with one elementary transducer, said clock causing the shifting of the contents of the respective said registers of N positions at a rate such that after each emission the transducers are connected in accordance with successive reception distributions corresponding with the path durations for the focal distance chosen.

In accordance with another aspect of the invention, the switching means are designed to change the reception connections after each transmission at a time which has alternately one or other of two delays with respect to the emission and to block the receiver during a predetermined period $\delta t$ after each switching.

The invention will be better understood from reading the description which follows of devices which constitute particular embodiments.

SHORT DESCRIPTION OF THE DRAWINGS

FIG. 5 is a block diagram of a circuit which may be associated with the transducers of FIG. 4;

FIG. 6 shows the pedestal removal effect due to the invention;

FIG. 7 is a partial diagram showing a modified embodiment of the circuit of FIG. 3 for attenuating switching noises;

FIG. 8 is a time diagram showing the signals which appear in operation at various points in the circuit of FIG. 7.

DETAILED DESCRIPTION OF PREFERRED EMBODIMENTS

Figure 1A:
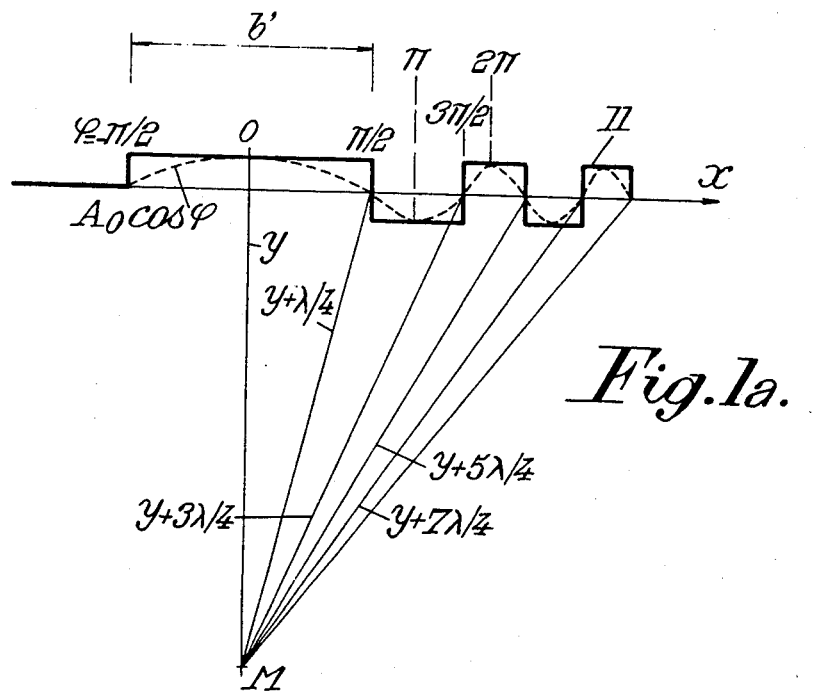
FIGS. 1a and 1b are diagrams showing the amplitude according to formulae (3) and (4) for focussing at point M, and simulation of that variation using a binary phase quantization.
Figure 1B:
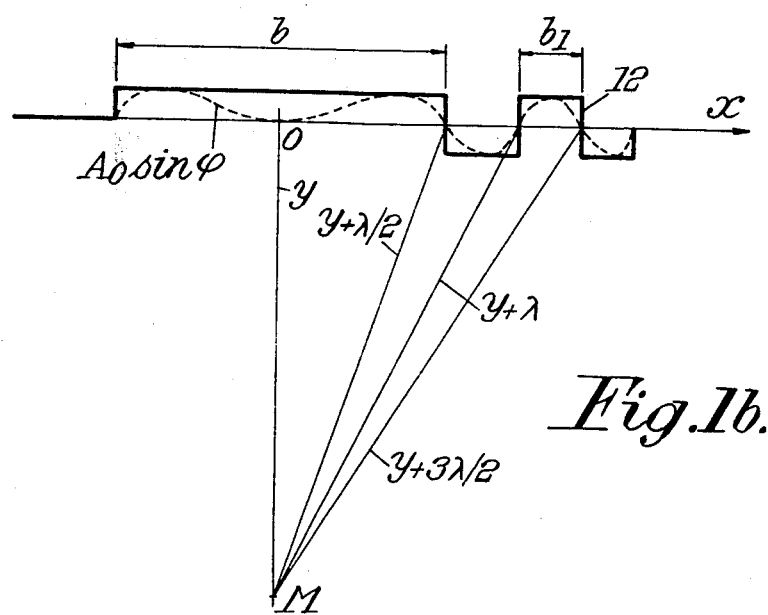

Referring to FIGS. 1a and 1b, there are illustrated methods for focussing the energy transmitted from or received by a linear array of elementary transducers at or from a point by simulating the actual phase distribution by one of the binary phase quantizations which are shown schematically by curves 11 and 12.

As indicated above, it has already been proposed to achieve a pseudo-focussing action by using, for transmission and reception, a group of elementary transducers over the whole width $b$ of the first Fresnel zone corresponding to formula (4). Formula (4) is selected rather than formula (3) since the first Fresnel zone corresponds to an amount of energy which is higher than that provided by the first Fresnel zone corresponding to formula (3), for which the width would be $b'$ lower than $b$.

It has already been suggested to use several groups of elementary transducers. A first group consists of transducers over the width $b$. The other transducers correspond to the width of the second Fresnel zone and possibly to further zones. On FIG. 1b, the width $b_1$ corresponding to the second zone has been illustrated. But the sizes of zones $b$ and $b_1$ have no direct relation. In other words, it is not possible to achieve exact simulation of widths $b$ and $b_1$ if elementary transducers of equal length are used. On the other hand, it is necessary that all elementary transducers have the same length along Ox if electronic scanning is to be achieved.

It is of interest to note that those skilled in the art would normally be led to feel that the best solution would consist to use the distribution illustrated in FIG. 1b, due to the potential advantage associated with the use of a central group of transducers over the length $b$ rather than $b'$. However, it has been found that such an assumption is not correct when several Fresnel zones are used, since the approximation which may be achieved using curve 11 (FIG. 1a) is substantially better than that of curve 12 (FIG. 1b).

According to the invention, a distribution corresponding to a plurality of Fresnel zones is used either for transmission or for reception and conversely a distribution corresponding to a lesser number of Fresnel zones (typically to a single zone) is used either for reception or for transmission, respectively.

Figure 2:
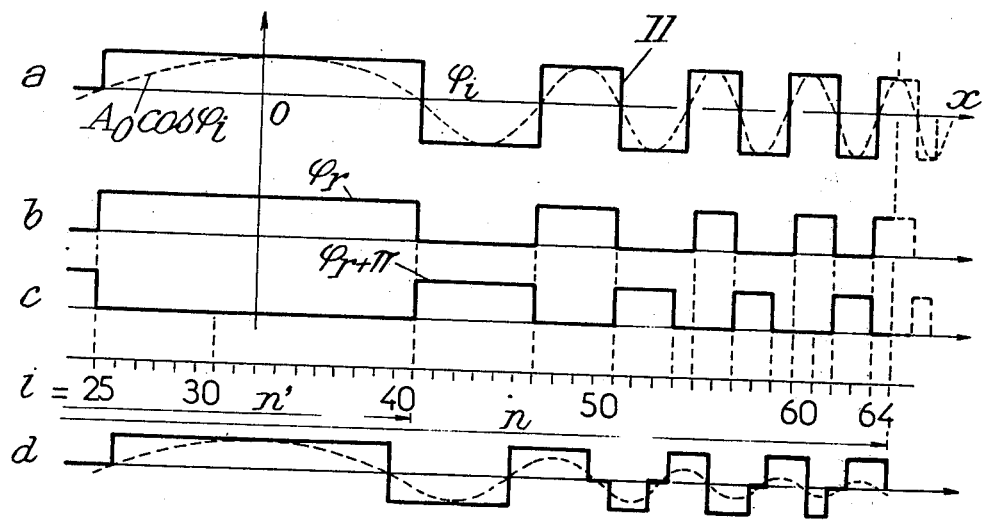
FIG. 2 shows the simulation of the phase distribution over sixty-four elementary signals transducers with binary phase quantization (line a) for focussing and how the distribution is achieved using two registers with sixty-four binary positions (lines b and c)

The first distribution may be achieved with only two phases and a phase difference of $\pi$, as illustrated on FIG. 2 (which corresponds to formula (3)).

Referring now to FIG. 2, the curve 11 corresponds to curve 11 on FIG. 1a and is an illustration of the theoretical distribution to be achieved on the transducers numbered from 24 to 64 in a group of $n = 64$ elementary transducers for focussing the transmission (or reception) at point M located on a line drawn perpendicularly to direction Ox from the junction between the elementary transducers numbered 32 and 33.

It may be seen that:

some of the $n$ transducers (line b) must receive the energizing signal with a reference phase $\phi_r$: this is the case with the transducers 25 to 40, 47 to 50, . . .;

other transducers must receive the signal with a phase shift equal to $\pi$ with respect to the reference phase (line c): these are the transducers 41 to 46, 51 to 56, . . .;

last, some transducers preferably receive no signal: (elementary transducers numbered $i = 54, 59$ and 65).

Conversely, focussing is likewise ensured from a point located at a distance $y$ by connecting the elementary transducers to a receiver with the phase distribution shown diagrammatically in FIG. 2. In another embodiment, schematized on FIG. 3, four different phases are used.

Figure 4:
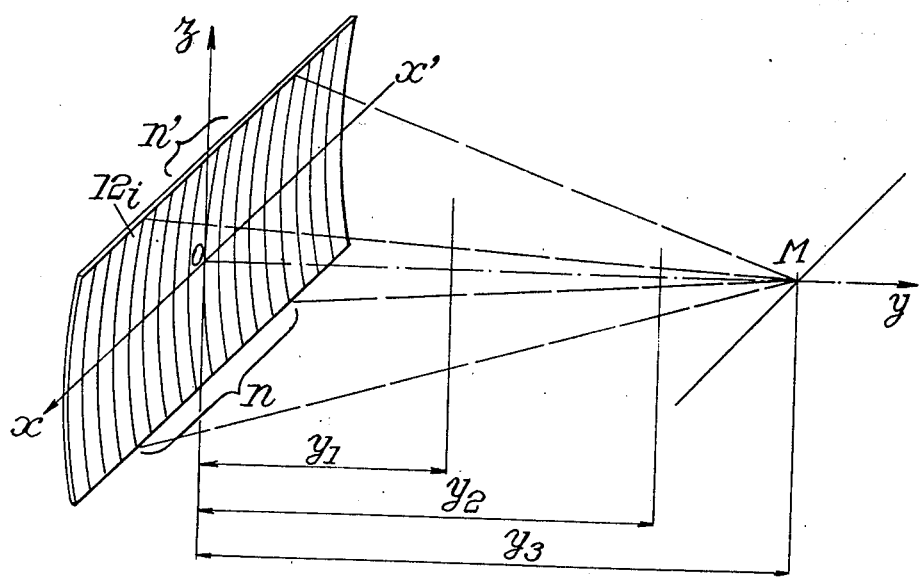
FIG. 4 shows diagrammatically a possible arrangement of N elementary transducers.

The distribution of lines $b-c$ in FIG. 2 may be achieved by means of a transducer system of the type shown diagrammatically in FIG. 4, associated with the circuit of FIG. 5, which enables scanning to be carried out along the direction $x'x$.

The transducer of FIG. 4 is designed to produce three-dimensional or space focussing at a point M and to effect electronic translocation or scanning along the direction $x'x$. To this end, it comprises elementary transducers shown diagrammatically by strips such as $12i$, in the form of part-circular segments, arranged over a cylindrical surface. The angular aperture of the cylindrical sector is selected to ensure sufficient concentration of energy at point M and to achieve satisfactory resolution in the direction of axis $z$. The N elementary transducers may be constituted by metal strips deposited by photogravure on the concave surface of a piezoelectric ceramic support in the form of a cylindrical segment whose convex surface is wholly coated with metal. When the pitch of the strips exceeds about 1mm, it is also possible to separate the strips by grooves cut out on a metal coated concave surface which have the advantage of producing mechanical uncoupling. Such transducers have a resonance frequency which may be adjusted during construction at a selected value and may be energized for transmission by a pulse generator.

Figure 3:
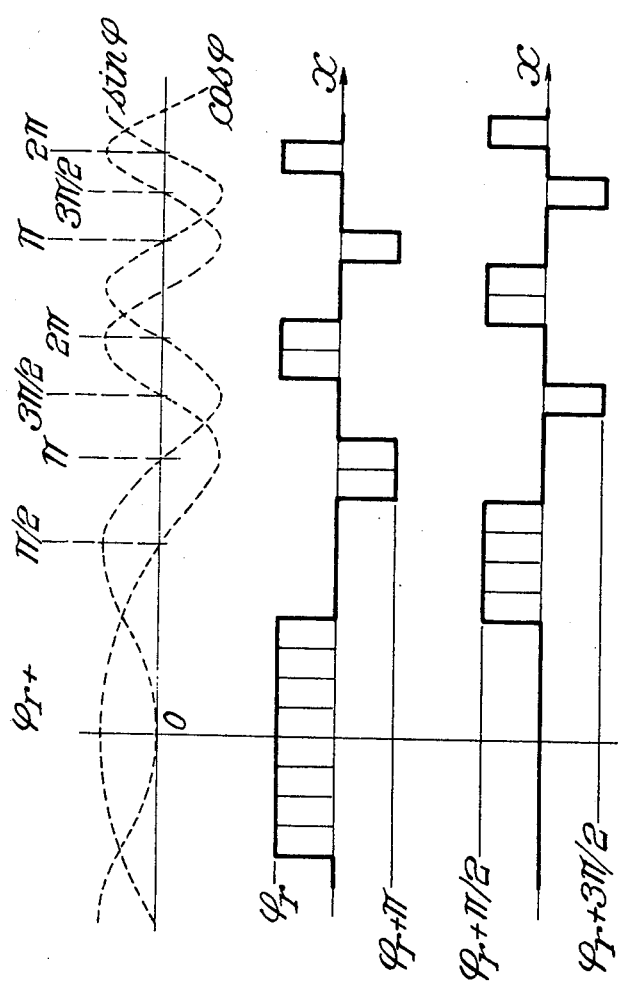
FIG. 3 is an illustration of the two terms of formula (2) and an approximation with a quantification of the phase at four levels (four quadrature waves)

The transducer system of FIG. 4 enables focussing to be achieved electronically at a point located at an adjustable predetermined distance from the transducer system when used in association with the circuit shown in FIG. 5 which is adapted to ensure pseudo-focussed transmission followed by reception with focussing at $p$ successive distances, $p$ being equal to 3 in the embodiment which will be described by way of example. In the embodiment of FIG. 3 a "geometrical" focussing obtained by arranging the elementary transducers along a cylindrical surface the centre of which is at a distance from the transducer system which is intermediate between $y_1$ (the shortest focal distance) and $y_3$ (the longest focal distance) is achieved in addition to "electronic" focussing.

Referring to FIG. 5, there is shown a circuit which includes, associated with each elementary transducer such as the only transducer $12i$ represented, switching means consisting of two switches $13i$ and $14i$ intended to connect transducer $12i$ to a single generator 15 or to a receiver system:

either with a reference phase $\phi_r$ (via switch $13i$), or with a phase differing by $\pi$ from $\phi_r$ (switch $14i$).

Switches $13i$ and $14i$ consist of field effect transistors the control electrode of which is connected to one position of a respective shift register so that the transistor is unblocked or blocked according to whether a binary 1 or a 0 occupies the position.

In the illustrated embodiment, intended for echography B, the connections are modified during an in-depth exploration in order to obtain a number of successive focussings taking into account the time for the ultrasonic waves to travel to and fro.

In the embodiment of the invention illustrated in FIG. 5, each of the registers 16 and 17 includes $p.N$ positions, $p$ designating the number of transducer distributions to be carried out for each in-depth exploration. It will be assumed that one transmission configuration and three reception configurations from points further and further away, which corresponds with $p = 4$, are to be carried out in succession.

The four phase distributions over $n$ successive elementary transducers are set in two fixed memories each including $p.n$ positions. The series output of each memory 18 or 19 is connected to the series input of the corresponding register 16 or 17. In particular, reprogrammable read only memories or "PROM" may be used.

Before operation, a proper sequence of binary 1's and 0's is written into the stores 18 and 19. That sequence is representative of the $p = 4$ distributions to be carried out so that there is found, starting from the output of store 18:

in positions $1, p+1, \ldots, (n-1)p+1$, the transmission distribution which will be assumed, for example, to be that causing energization, with the reference phase, of the $n'$ elementary transducers of serial numbers 25 to 40 (FIG. 1). The elementary transducers to be energized will be represented by binary 1's introduced into the corresponding positions, the transducers which will not receive energy being represented by 0's;

in positions $2, p+2, \ldots, (n-1)p+2$, the distribution corresponding with the focussing for reception from the shortest distance, designated by $y_1$ in FIG. 4;

in positions $3, p+3, \ldots, (n-1)p+3$, the distribution corresponding with focussing at distance $y_2$;

finally, in positions $4, p+4, \ldots, (n-1)p+4$ (that is to say, for $p = 4$, the positions $4, 8, \ldots, 4n$), the distribution corresponding with focussing at the greatest distance $y_3$.

If, for example, the distribution corresponding with the distance $y_2$ is that shown on line $a$ on FIG. 2, the distribution corresponding with the distance $y_1$ will be of the type of line $d$.

Once the repartition has been loaded into the memories and transfer has taken place, the four configurations indicated are found in the registers 18 and 19, the bits representative of $i_o, i_1, i_2$ and $i_3$ (the bits identifying the four phases to be associated with transducer $i$) being found in successive positions of the registers as indicated in FIG. 5.

Generator 15 may be entirely conventional. More specifically, it may consist of a triggered oscillator (for instance type 74 124 oscillator manufactured by TEXAS INSTRUMENTS) followed by a transistorized amplifier if needed for delivering the necessary power. A pulse generator (for instance TEXAS 74 121 univibrator) may as well be used if the transducers are of the dampened resonant type. Generator 15 feeds all transistors $13_1, \ldots, 13_i, \ldots 13_N$ and $14_1, \ldots, 14_i, \ldots, 14_N$ which constitute the switching means, by way of an electronic switch 28 and means providing, from the input signal, two signals out of phase by 180°. The phase shift means represented in FIG. 5 consists of a transformer 20 with its midpoint earthed and the opposite polarities of which are applied, one to all of the transistors 13, the other to all of the transistors 14. The oscillator 15 includes a control input 21 connected to a time base 22 which fixes the rate of transmission of the trains of ultrasonic waves and of the electronic scanning which occurs after each transmission-reception sequence. A sequencer 23 for controlling the rate of operation receives at its input 24 the clock output pulses, shifts the registers contents and resets the registers 16 and 17 after each complete scanning sequence.

The reception channel comprises, starting from transformer 20 and switch 28, an amplifier 26 and a circuit 27 for processing and displaying the data which may be of type which is conventional in echography B. The electronic switch 28 protects the reception channel against the transmission signals. Display may be effected on a CRT with horizontal sweep for distance, analogical representation of the echoes and skip from one line to the next line of the frame after each in-depth probing.

Since operation of the device appears from the above, it will only be briefly indicated. When the whole of the original contents of the stroes 18 and 19 has been passed into the registers 16 and 17 to which the transistors 13 and 14 are connected contain bits corresponding with the transmission configuration. An in-depth exploration starts off with a pulse supplied by the clock to the oscillator 15 and to the sequencer 23. The oscillator 15 emits in response a short signal pulse.

At the end of a first time interval $\tau_1$, chosen to be less than the to and fro time for the distance $y_1$, sequencer 23 emits at its output 30 a forward shift control pulse which is applied to registers 18, 19, 16 and 17. The positions of the registers 16 and 17 to which the transistors 13 and 14 are connected then receive bits representative of the distribution leading to focussing at distance $y_1$. At the same time, the electronic switch 28 is actuated by a circuit (not shown) and switches the echoes, if any, towards the reception channel. High resolution is thus obtained for echoes from low depth.

At the end of a second time period $\tau_2$, less than the to and fro time for the distance $y_2$, another forward shift control pulse appears at output 30 of the sequencer; another configuration becomes present in the positions of the registers 16 and 17 connected to the transistors $13_i$ and $14_i$, which corresponds to focussing at distance $y_2$.

Finally, at the end of an interval of time $\tau_3$, less than the to and fro time for the distance $y_3$, another pulse again changes the distribution applied to the transistors $13_i$ and $14_i$. In order to re-initiate the cycle, a last pulse supplied by the sequencer 23 to the registers re-applies the transmission configuration onto the transistors $13_i$ and $14_i$ but with a shift of one transducer towards the right. The time interval $\tau_4$ between the transmission of the short dampened ultrasonic waves and the sending of the last pulse by the sequencer 23 is selected so that all echoes capable of occuring in the depth being explored have been received.

Finally another pulse sent by the clock 22 to the oscillator 15 and to the sequencer 23 causes another in-depth exploration.

It may be seen that at the cost of moderate increase in the length of the registers, focussing of reception at variable depth is obtained, which considerably increases the possibilities offered by the device, especially in echography B (also designated as B-scan). Furthermore the association of this focussing at variable depth for the reception with transmission from a linear array of elementary transducers fed in phase enables the signal received to be "apodized" at the cost of a decrease of the resolution which remains quite acceptable. This result appears in FIG. 6. In FIG. 6, the upper diagram shows the reception curve 32 (amplitude as a function of the distance) in the case of a configuration of the type shown in FIG. 2; the curve exhibits, besides the central lobe, two distant secondary lobes which may give rise to parasitic reflections if the secondary lobes correspond with highly reflective obstacles.

The middle diagram shows the transmission curve 33 of a transducer system consisting of elementary transducers which are fed in phase (for example, transducers numbered 25 to 40 in FIG. 2). It may be seen that the central lobe is much wider and hence corresponds with lower definition but, as a counterpart, the curve has no secondary lobes.

Finally, the curve 34 of the lower diagram of FIG. 6 represents the transmission-reception curve of a device of the type which has just been described. The ordinate of every point on this curve corresponds with the product of the ordinates of the curves 32 and 33 for the same distance from the array. It may be seen that "apodization" is obtained while the resolution is only very slightly diminished with respect to that of curve 32.

The circuit shown in block diagram form in FIG. 5 includes a reception channel which collects all the signals transmitted by the switch 28. In certain cases, the switching operations necessary during an in-depth exploration appear as noise which is recorded on the display screen in the form of a bright line which is a nuisance to the observer. That bright line may be suppressed by inserting in the reception channel an analogic gate which is normally enabled but which is disabled during a short time interval starting from each switching. But this procedure causes the echoes to disappear which may occur during time periods of blocking of the gate.

That difficulty is overcome in the modified embodiment of the invention which uses, instead of a single time interval $\tau$, from the transmission, two intervals $\tau$ and $\tau'$, one for scanning of odd order, the other for scanning of even order. Thus the switching noises are totally adverted, whilst avoiding total suppression of the echoes occuring during the blocking periods.

The circuit illustrated diagrammatically in FIG. 7 enables this result to be attained. This diagram is shown only for the purpose of explanation and could be simplified. Operation is shown diagrammatically in FIG. 8 where each line is allocated a reference number and shows diagrammatically the signals which appear at the points in FIG. 7 allocated the same numbers. The time base 22 feeds in parallel four univibrators or single shots 35, 36, 37 and 38. The univibrators 35 and 36 provide at their output signals for forward shift of the registers at the end of fixed time intervals $t_0$ and $t_1$ starting from the emission of a pulse by the clock 22. Univibrators 37 and 38 provide pulses at the end of intervals of time which are alternately equal to $\tau_2$ and $\tau_3$, then $\tau'_2$ and $\tau'_3$. The alternation of the intervals of time may be obtained very simply by means of flipflops 39 and 40 which block and unblock alternately a field effect transistor for inserting or short-circuiting a supplementary resistor in the RC circuit of the univibrators 37 and 38.

The time intervals $\tau_2$ and $\tau'_2$ are selected to be greater than the to and fro time for the focal distance $y_1$ and lower than the to and fro distance for the focussing $y_2$. Similarly, the time intervals $\tau_3$ and $\tau'_3$ are designed to lie between the to and fro times for $y_2$ and $y_3$ (FIG. 8).

Each univibrator 35, 36, 37 and 38 feeds a univibrator 41 of fixed duration $\delta t$ corresponding with the duration sought for the blocking gate. A set of OR-gates 42, 43 and 44 applies on the control input of an analogic gate 45 all blocking time gates controlled by the univibrators 35, 36, 37 and 38. The analogic gate is interposed between unit 20 and amplifier 26.

Operation of the device appears in FIG. 8.

At the end of time interval $\tau_1$ starting from the pulse emitted by the clock 22, the univibrator 35 causes a forward shift of the registers in order to change over from the transmission configuration to the configuration for focussing at the distance $y_1$. At the same time a square pulse of duration δt appears at the output from the OR-gate 43 and disables analog gate 45.

The time interval $\tau_1$ may be sufficiently short to correspond with a distance less than the boundary of the zone to be explored closest to the transducers. Under these conditions, the suppression of echoes, if any, in this zone has no troublesome consequences.

At the end of a time interval $\tau_2$ (or $\tau'_2$), the univibrator 37 in turn applies a shift pulse to the registers and a pulse for blocking the gate 45 through the OR-gate 42. There is a shift of the "blind" zones associated with any in-depth probing and the next without overlap between these zones (represented one in full line and the other in dashes on line 42 in FIG. 8).

The univibrator 38 operates in the same way as univibrator 37 with a time delay which is alternately $\tau_3$ or $\tau'_3$.

Last, the return to the transmission configuration occurs at the end of an interval of time $\tau_0$. This interval $\tau_0$ may be sufficiently long for the corresponding blocking time gate (line 53 in FIG. 6) to correspond with a distance greater than that of the rear boundary of the zone to be explored in depth. This "unabling" or blocking gate may be immediately before the transmission of another train or ultrasonic waves.

By way of example, it may be indicated that two devices in accordance with the invention have been produced for the display of the cardiac muscle by echography B or "B-scan".

The first device included $N = 80$ transducers with reception on 32 elementary transducers and sweeping at 50 frames per second, enabling storage of television type. The focal depths $y_1$, $y_2$ and $y_3$ were respectively about 2.5 cm, 5cm and 10cm.

In another device with a slower operating rythm (25 frames per second), $N = 160$ elementary transducers have been employed, with focussing ensured by means of $n = 64$ transducrs.

It must further be observed that the device which has just been described may be employed in four different ways, which enables the most advantageous to be selected in each case:

transmission and reception with in-phase use of all the elementary transducers (without actual focussing), transmission with elementary transducers energized in phase and reception with focussing at only one depth, transmission and reception with focussing at only one depth, especially for echography C, finally, transmission with in-phase energization of the elementary transducers and distribution for focussing at a depth adjusted during the scanning, that is to say, with a result which may be compared with that from the technique called "tracking focussing" but with simpler means.

In the last embodiment, with the numerical data mentioned above, there is obtained a field depth which extends from the immediate proximity of the transducer system up to about 20 cm.

Numerous modified embodiments of the invention may be used.

In particular, shift registers 16 and 17 having only N positions may be provided and the stores 18 and 19 with pn positions be replaced by $p$ stores in parallel, each having $n$ positions. The first store contains the reception configuration corresponding with focussing at the nearest distance and so on. In this case, it is necessary to employ a fast clock and a digital system enabling the following sequence to be carried out for each in-depth exploration:

shift to the contents of the first store of each of the sets so as to transfer their contents into $n$ corresponding successive positions of the shift registers 16 and 17 having N positions;

transmission of a train of ultrasonic pulses;

shift of the contents of the second store of each set in order to cause replacement of the transmission configuration by the reception configuration with focussing at the nearest distance, in the shift registers 16 and 17;

shift of the contents of the third store of each set, and so on;

the sequence then repeats, but with displacement by one position in the shift registers 16 and 17, of the group of $n$ positions which receives the successive distributions.

This approach involves the use of a fast clock and a more complex logical circuit than the preceding one, while it has the advantage of necessitating only shift registers with N positions instead of pN positions.

Numerous modified embodiments may be used. For instance, a phase distribution as illustrated in FIG. 3 may also be achieved, but requires four switching elements per transducer and phase lag means adapted to provide a signal which is $\pi/4$ out of phase with respect to a reference signal. On the other hand, the phase lag means that consist of a single unit (delay line for instance) rather than a large number of such units providing different delays in the prior art.

I claim:

1. A device for ultrasonic imaging with electronic scanning, having an array of N identical elementary transducers distributed at equal intervals along a scanning direction and operating at frequency $f$; a signal generator for generating electrical signals; a signal receiver for receiving and processing electrical signals; means for storing an electrical phase distribution signal representative of the phase distribution of $n$ signals associated with $n$ adjacent transducers of said array, $n$ being an integer greater than 1 and less than N, each said signal having a frequency $f$ and having any one of $m$ phases with respect to the remaining said $n$ signals ($m$ being an integer less than $n$), said electrical phase distribution signal being determined so that said $n$ adjacent transducers focus energy at a point located at a predetermined distance from said array of transducers; switch means for simultaneously and temporarily connecting said generator or receiver to a set of $n$ transducers in accordance with said phase distribution and subsequently or previously for simultaneously and temporarily connecting said receiver or generator to those $n'$ transducers among the $n$ transducers which are closest to said point to said receiver; and sequencing means for causing said switch means to connect said generator and receiver, successively to sets of $n$ and $n'$ transducers which are each time shifted by at least one said transducer such that scanning occurs throughout said array.

2. A device according to claim 1, wherein $n'$ is selected to correspond with the first Fresnel zone or the phase distribution ensuring focussing at the predetermined distance.

3. A device according to claim 1, wherein the switching means are designed to change the reception connections after each emission at a time which has alternately one or other of two delays with respect to the emission and to block the receiver during predetermined period $\delta t$ after each switching.

4. A device according to claim 3, wherein the switching means are designed to modify only the delay corresponding with the reception configurations other than those intended for focussing at the nearest distance and for focussing at the furthest distance.

5. A device according to claim 1, wherein $m$ is two and some of the transducers will receive the energy with a first reference phase and the others energy with a second phase which is 180° out of phase with the reference phase.

6. A device according to claim 5, wherein the storage means include two sets of shift registers, each set comprising a first shift register intended to store the location of those of the $n$ elementary transducers to be connected to the generator with the first or the second phase, respectively, a second shift register intended to store the location of those of the $n$ elementary transducers to be connected to the receiver with the first or second phase for achieving focussing at a predetermined distance from the line, and if necessary other shift registers intended to store the location of the $n$ elementary transducers to be connected to the receiver with the said first or second phase for achieving focussing or fucussings at another predetermined distance or at other predetermined distances; a clock being provided for causing the shifting of the contents of the first register and its transfer in series into $n$ successive predetermined positions of a shift register of N positions, each position controlling the switching means associated with one elementary transducer, and then for causing the shifting of the contents of the second register and its transfer in series into the same positions of the shift register of pN positions, and so on, and for recommencing the shift sequence by making the group of $n$ positions advance by one position in the shift register of N positions.

7. A device according to claim 5, wherein the transducers are connected to simulate a $A_o \cos\phi$ Fresnel distribution.

8. A device according to claim 5, wherein the storage means include two shift registers having p.n positions, which store, in operation:

the first, in positions $1, p, 2p, \ldots, (n-1)p$, the location of those of the $n$ elementary transducers to be connected to the generator with the first phase; in the positions $2, p+1, \ldots, (n-1)p+1$, the location of those of the $n$ elementary transducers to be connected to the receiver with the first phase for achieving focussing at a first predetermined distance from the line; and if necessary, in a group or other groups of $n$ positions, the location of the $n$ elementary transducers to be connected to the receiver with the said first phase for achieving focussing or focussings at another predetermined distance or at other predetermined distances;

the second, in the positions $1, p, 2p, \ldots, (n-1)p$, the location of those of the $n$ elementary transducers to be connected to the receiver with the second phase; in the positions $2, p+1, \ldots, (n-1)p+1$, the location of those of the $n$ elementary transducers to be connected to the receiver with the second phase for achieving focussing at a second predetermined distance from the line; and if necessary, in a group or other groups of $n$ positions, the location of the $n$ elementary transducers to be connected to the receiver with the said second phase for achieving focussing or focussings at the other predetermined distance or at other predetermined distances; a clock being provided for causing the shifting of the contents of the said registers and their transfer in series into two shift registers of N positions, each position controlling the switching means associated with one elementary transducer, said clock causing the shifting of the contents of the respective said registers of N positions at a rate such that after each emission the transducers are connected in accordance with successive reception distributions corresponding with the path duration for the focal distance chosen.

9. A device according to claim 8, wherein the transmission distribution of the transducers corresponds with the first Fresnel zone for focussing at an average distance among the various predetermined distances, starting from the array, in number greater than 1.

* * * * *